United States Patent [19]

Nankai et al.

[11] Patent Number: 5,320,732

[45] Date of Patent: Jun. 14, 1994

[54] BIOSENSOR AND MEASURING APPARATUS USING THE SAME

[75] Inventors: Shiro Nankai, Hirakata; Mariko Kawaguri, Moriguchi; Toshihiko Yoshioka, Osaka; Haruhiro Tsutsumi, Ehime; Minoru Fukuda, Matsuyama, all of Japan

[73] Assignee: Matsushita Electric Industrial Co., Ltd., Osaka, Japan

[21] Appl. No.: 75,859

[22] Filed: Jun. 11, 1993

Related U.S. Application Data

[63] Continuation of Ser. No. 732,720, Jul. 19, 1991, abandoned.

[30] Foreign Application Priority Data

Jul. 20, 1990 [JP] Japan .................................. 2-193645

[51] Int. Cl.$^5$ .............................................. G01N 27/26
[52] U.S. Cl. ...................................... 204/403; 204/406
[58] Field of Search ........................... 204/403; 435/817

[56] References Cited

U.S. PATENT DOCUMENTS 4,654,127 3/1987 Baker et al. ........................ 204/406
4,999,582 3/1991 Parks et al. ........................ 204/406
5,064,618 11/1991 Baker et al. ........................ 204/407
5,096,669 3/1992 Lauks et al. ........................ 204/403

Primary Examiner—John Niebling
Assistant Examiner—Bruce F. Bell
Attorney, Agent, or Firm—Ratner & Prestia

[57] ABSTRACT

The subject invention provides a simple sensor and an easy to handle biosensor measuring apparatus for the purpose of making measurements easily, rapidly and with high accuracy for specific components within a biological specimen such as blood.

The biosensor of the subject invention is provided with a protrusion or a depression in a portion of a base having at least a measurement electrode and an opposing electrode. Also, the biosensor measuring apparatus is so configurated to have a mating means in the main body of the measuring apparatus freely supporting this biosensor to contact the said sensor's protrusion or depression, and further having the activating switch of the driving power supply located in this mating means.

By means of these, it is possible to prevent wasteful measuring operations, as noted in the prior art biosensors, such as inserting the sensor backwards and making measurements with the sensor inserted backwards.

6 Claims, 5 Drawing Sheets

BIOSENSOR AND MEASURING APPARATUS USING THE SAME This application is a continuation of application Ser. No. 07/732,720 filed Jul. 19, 1991, now abandoned.

BACKGROUND OF THE INVENTION

In the context that in recent years various biosensors utilizing singular catalytic action of enzymes have been developed and are undergoing clinical trial applications, demand exists for biosensors capable of making rapid and highly accurate measurements.

Taking glucose sensors as an example, today when there is a marked increase in the number of persons afflicted with diabetes, the measurement and management of blood sugar require extremely complicated steps if blood were to be centrifuged to make measurements of the plasma as done traditionally and there is a demand for a sensor capable of making measurements from whole blood.

As a simple type, there is one, similar to the test paper used in testing urine, of using a stick-shaped support and placing thereon a medium containing an enzyme reacting only to a sugar (glucose) and a dye which changes at the time of enzyme reaction or due to the products of enzyme reaction. The method is to drip blood on this medium and to measure changes in the dye after a given period of time, either with the naked eye or optically, but there is much hindrance from colored substances in the blood and the accuracy is low.

On one hand, there are proposals for devices which, including the electrodes, can be thrown away after each measurement, but while making measurement operations extremely simple, from the standpoint of electrode materials, such as platinum, and their structure, they cannot avoid becoming very expensive devices. Also, while sputtering method or vapor deposition method can be used for manufacturing the platinum electrodes, they will be very expensive to manufacture.

As a throw-away method including the electrodes, a biosensor was proposed in the Laid Open Patent Application SHO 61-294351. This biosensor, as shown in FIG. 9, has an electrode system 30 (30'), 31 (31') and 32 (32') formed from such material as carbon by a method such as screen printing upon an insulating base 37, and after forming an insulating layer 33, the electrode system is covered by a multi-apertured medium 35 holding an oxidoreductase and an electron receptor, and the whole is unitized with a support 34 and a cover 36.

When a sample fluid is dripped onto the multi-apertured medium the oxidoreductase and the electron receptor held by the multi-apertured medium are dissolved by the sample fluid, enzyme reaction proceeds between the substrates in the sample fluid and the electron receptor is reduced. After the reaction is completed, the reduced electron receptor is electrochemically oxidized and the substrate concentration within the sample fluid is obtained from the value of oxidation current at that time.

In the above noted measurement, a given voltage is provided to the sensor's electrode system, the current flowing between the electrodes is measured, and the substrate concentration in the sample fluid is calculated on the basis of this signal.

In prior art structure such as that given above, wasteful measuring work occurred such as inserting the throw-away sensors backwards and even making measurements with sensors inserted backwards. Hence, there is desire for a simple sensor and easily manipulated biosensor device to simply, rapidly and highly accurately measuring specific components within a biological specimen such as blood.

SUMMARY OF THE INVENTION

The subject invention forms a biosensor by providing, a projection or a depression on one part of a base material having at least a working electrode and a counter electrode in the housing itself, which supports this biosensor during insertion, extraction and in between, a mating portion consisting of a groove, a depression or a projection is provided to mate with the said projection or depression only when the sensor is inserted in the prescribed direction, to form a biosensor measuring apparatus further having an activating switch in the mating portion.

Thus, by providing a projection or a depression, it is possible to prevent the error of inserting the sensor backwards into the device, and have the activating switch of the device operate only when insertion is made in the prescribed direction.

DETAILED DESCRIPTION OF THE INVENTION

The subject invention is related to a biosensor and biosensor measuring apparatus capable of rapidly and easily determining with high accuracy a specific component within various biological specimens.

The subject invention is a biosensor characterized by the provision of a protrusion or a depression in a portion of the sensor for the purpose of preventing backward insertion.

Also, the subject invention is a biosensor measuring apparatus characterized by having, in the main body freely supporting a sensor provided with a protrusion or a depression for preventing backward insertion, mating means consisting of a groove or a depression or a protrusion mating with the said protrusion or depression only when the said sensor is inserted in the specified direction.

Furthermore, the subject invention is a biosensor measuring apparatus characterized by provision of a switch which turns on the driving power source by the insertion of the sensor into the connector, which is the insertion aperture for the sensor.

In the subject invention, the reverse insertion of the sensor is prevented by a simple structure and an error in the direction of its insertion is recognized without activating the apparatus.

Figure 1:
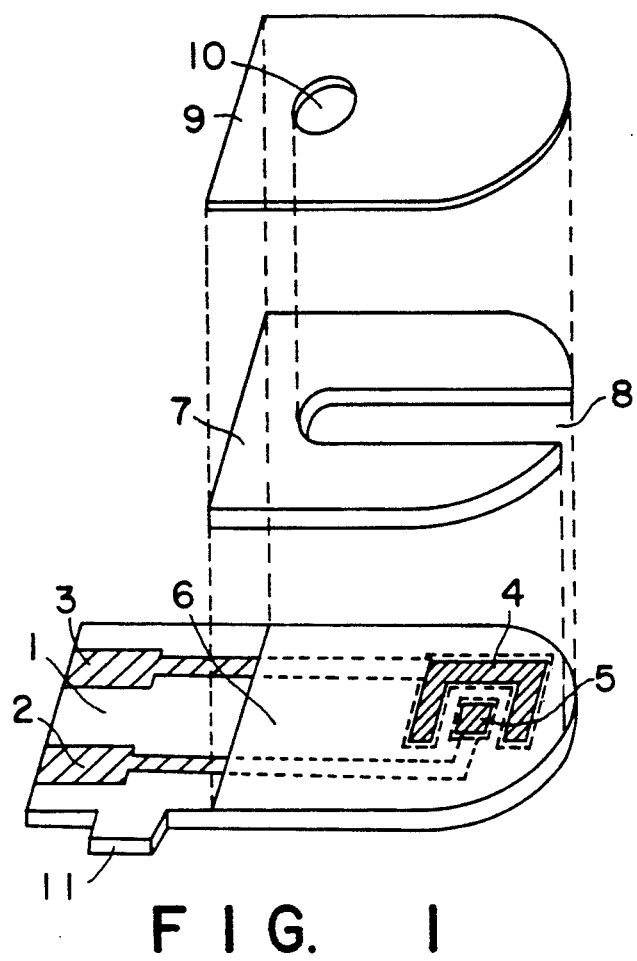
FIG. 1 is an exploded slant view of a biosensor in one embodiment of the subject invention.
Figure 2:
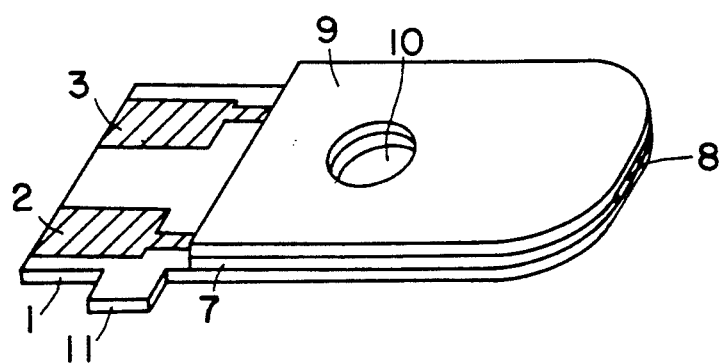
FIG. 2 is an external slant view of a biosensor in one embodiment of the subject invention.

The details of the subject invention will be given in the following together with its embodiments. FIG. 1 is an exploded slant view of the biosensor and FIG. 2 is its external slant view. Atop the base 1 are an counter electrode 4 and a working electrode 5, lead 3 and lead 2 connected to same and an insulating layer 6. Also, while not shown in the figures, a reaction layer is formed to cover the counter electrode and the working electrode containing an enzyme and mediator (electron receptor). A cover 9 is affixed above the base 1 over a spacer 7. 8 is the sample supply hole, and from here the fluid to be tested (specimen) is introduced above the counter electrode and the working electrode by means of the capillary effect. With the introduction of the fluid to be tested, the air within is expelled through air hole 10. 11 is an inverse insertion preventing protrusion to prevent backward insertion, and by this protrusion it is possible to prevent the backward insertion into the biosensor apparatus itself, as related below.

Figure 3:
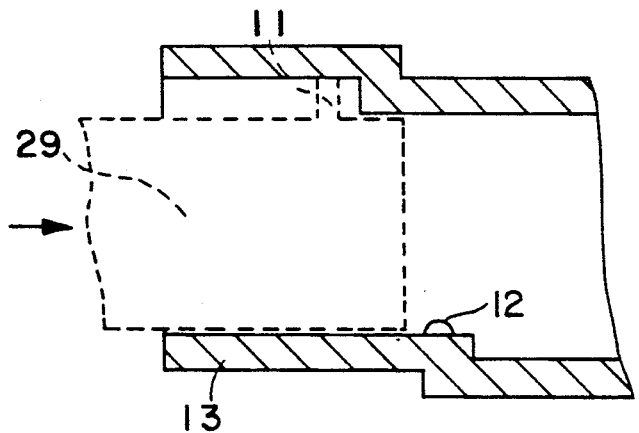
FIG. 3 is a simulated cross-section view of the mating portion of the biosensor and the biosensor measuring apparatus itself in one embodiment of the subject invention.

Also, FIG. 3 shows a state where the sensor 29 is inserted into the connector 13 of the apparatus itself (not shown) from the direction shown by the arrow, and the apparatus itself can freely support the sensor. In the figure, 12 is the switch deposed in the mating portion and is ganged to the driving power supply. Clearly, if the biosensor were flipped about a central axis stretching from the front ent to the back end, an attempted insertion would result in a tip portion of the biosensor contacting the protruding wall of connector 13 so to prevent further insertion and, consequently, prevent activation of switch 12.

Figure 8:
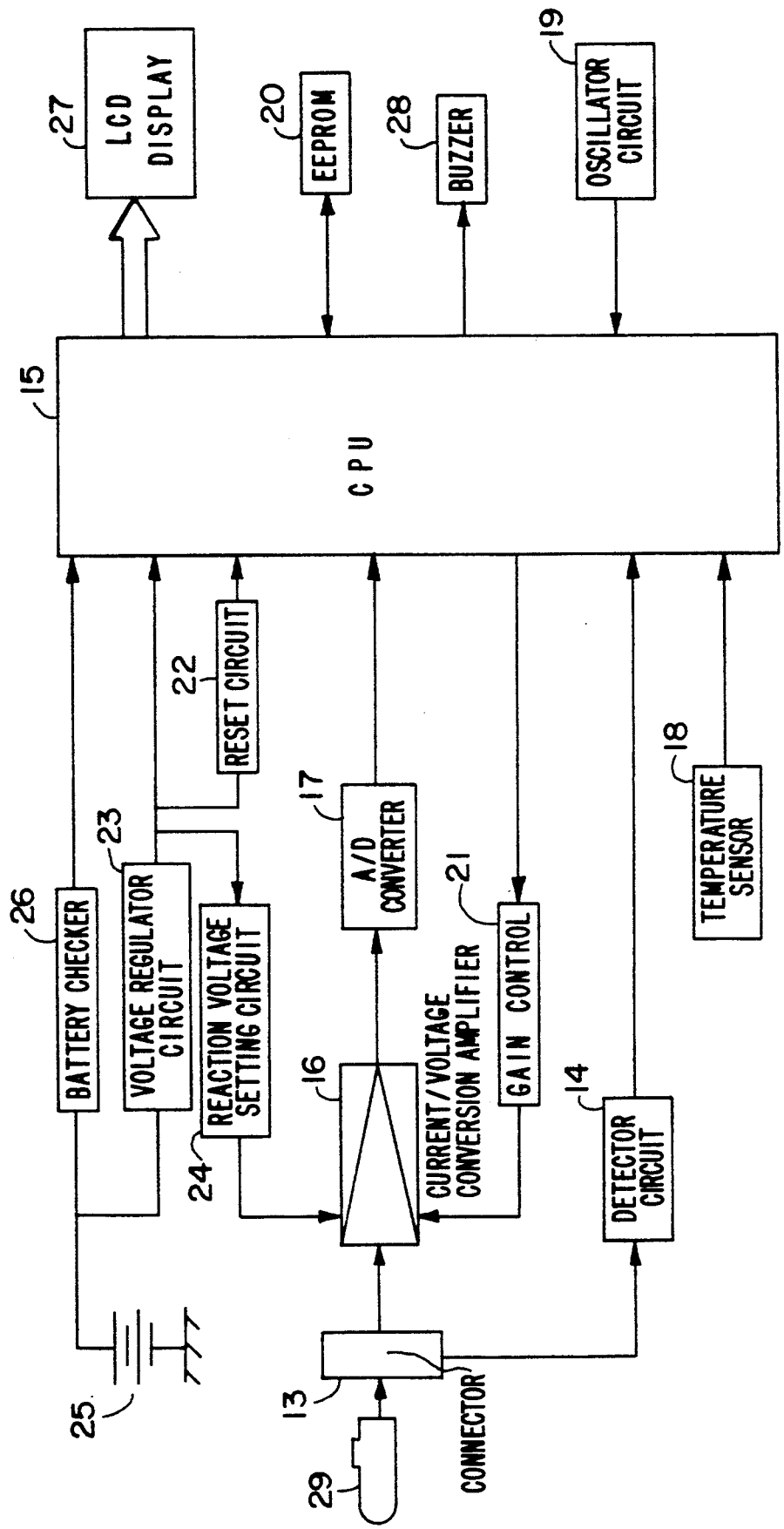
FIG. 8 is a block diagram of the control system of the biosensor measuring apparatus of an embodiment of the subject invention.
Figure 9:
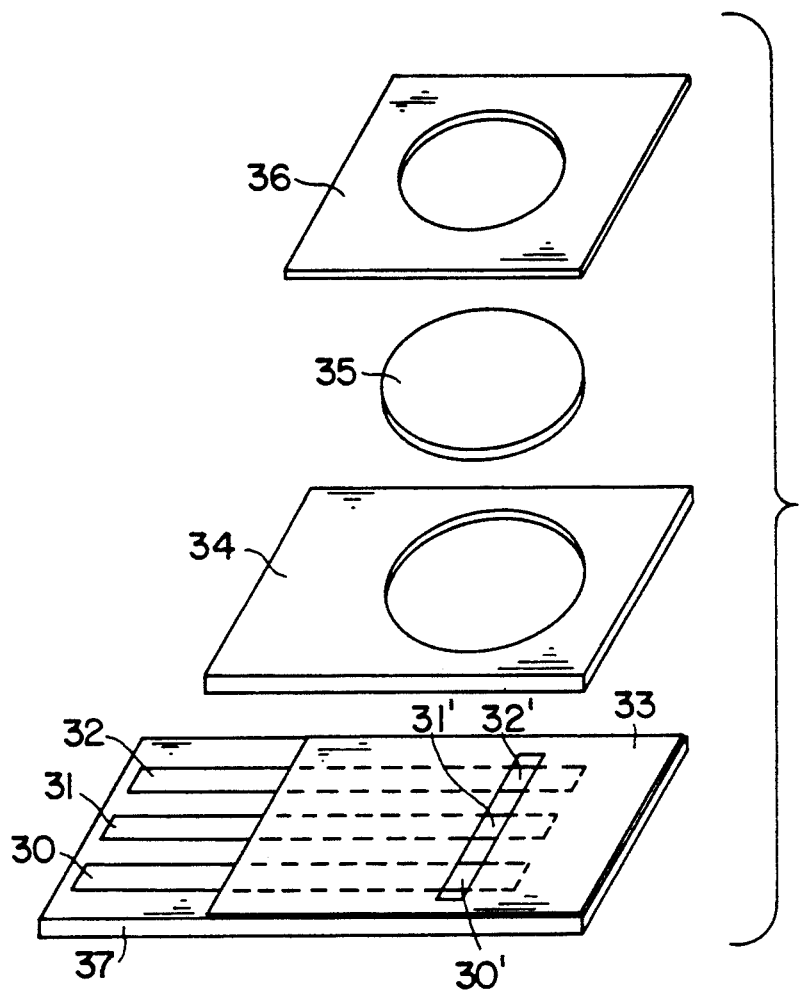
FIG. 9 is an exploded slant view of a prior art biosensor.

FIG. 8 is a block diagram of the control system of the subject invention's biosensor apparatus. The measurement steps using this apparatus are as follows.

First, when sensor 29 is properly inserted into the connector of the main body, switch 12 activates the driving power supply, the insertion of the sensor 29 is detected by the detector circuit 14 and through the CPU 15 components such as the current-voltage conversion amplifier 16, the A/D converter 17 and the temperature sensor 18 are turned on.

Next, when the fluid to be tested is introduced into the sensor this is detected and the measurement is commenced. After reaction takes place for a given time, a voltage is applied between the working electrode and the counter electrode via the reaction voltage setting circuit 24.

The signal obtained by the measurement is converted into concentration (in the sample) by the signal processor composed of the CPU 15, etc., and is displayed on the LCD display 27.

The driving power supply of the measuring apparatus is composed of the battery 25, etc., and power is supplied via the voltage regulator circuit 23, checking the voltage by the battery checker 26. Also, 28 is a buzzer indicating the progress of the measuring operation, 19 is a signal generator circuit generating a pulse which is the operating clock of the apparatus, and 22 is a circuit which resets the CPU when, for instance, the measurement is halted while in progress. 20 is a memory (such as an EEPROM) for storing the compensating values, etc., for each apparatus.

In the above, the interior wall of the connector is stepped and if the sensor is inserted backwards the protrusion for preventing reverse insertion touches the stepped portion and the sensor will not go in to the specified position so that mis-insertion is visually noticeable. Also, in this case, the sensor will not press on the operating switch 12 either so that the apparatus will not operate.

What is meant by erroneous direction of insertion is when front and back is reversed, or when an insertion is attempted via the sample supply hole which is in the opposite direction from the lead portion. In either case, by providing a protrusion or a depression in a portion of the base, the apparatus can be made to operate only when the insertion is made from the specified direction.

Moreover, other embodiments are shown in FIGS. 4 and 5 and FIGS. 6 and 7.

Figure 4:
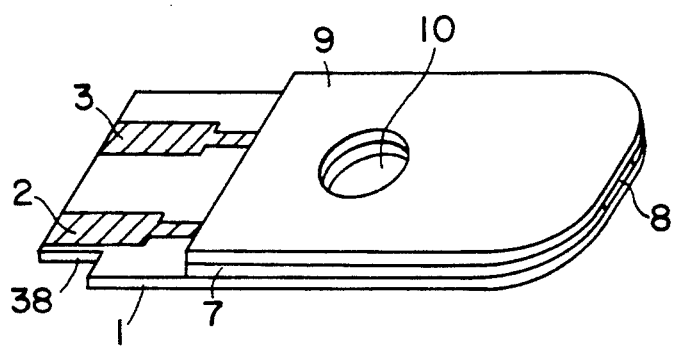
FIG. 4 is an external slant view of a biosensor in another embodiment of the subject invention.
Figure 5:
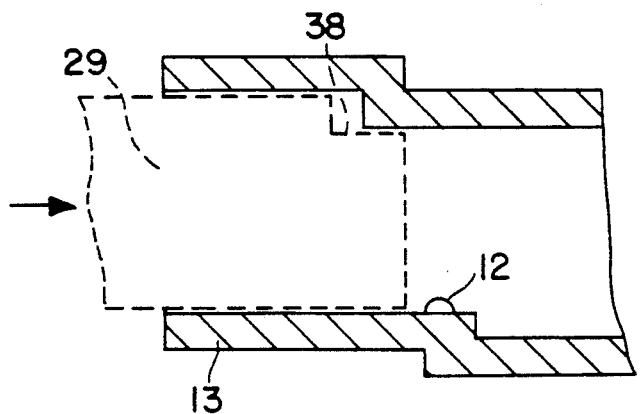
FIG. 5 is a simulated cross-section view of the mating portion of the biosensor and the biosensor measuring apparatus itself in another embodiment of the subject invention.

FIG. 4 shows an example where a depression 38 is provided at a corner near the sensor base's leads. FIG. 5 shows the state where the sensor has been inserted in a connector having a mating portion to mate with this depression.

Figure 6:
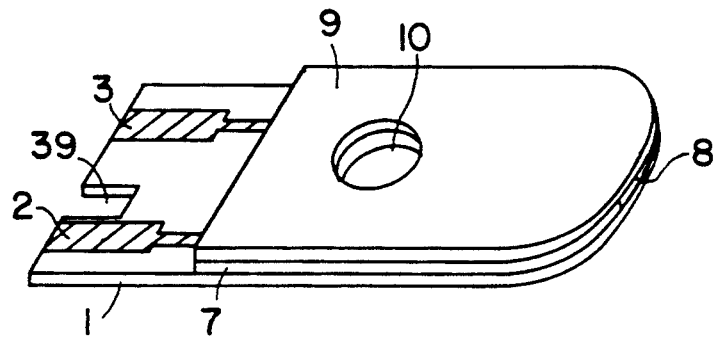
FIG. 6 is an outside slant view of the biosensor in another embodiment of the subject invention.
Figure 7:
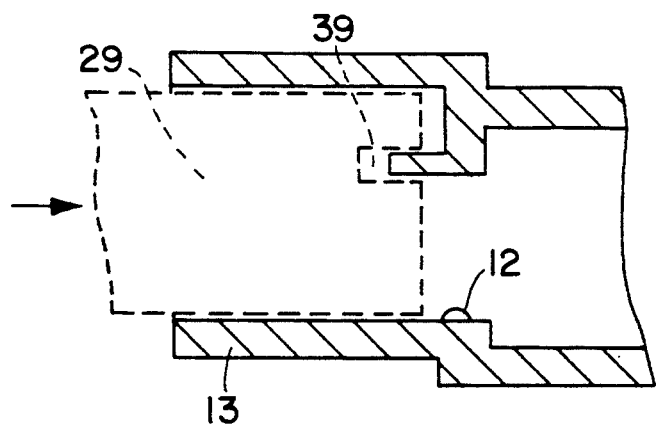
FIG. 7 is a simulated cross-section view of the mating portion of the biosensor and the biosensor measuring apparatus itself in another embodiment of the subject invention.

FIG. 6 shows the case where a depression 39 is provided near the middle of the lead portion of the base. FIG. 7 shows the state where the sensor has been inserted into a connector having a mating portion to mate with this depression. As shown in FIGS. 6 and 7, depression 39 (or alignment control slot) is disposed off center in the front end of the base.

As shown in the above embodiments, by providing the biosensor with a protrusion or a depression and by providing a mating portion in the main body of the biosensor apparatus to mate with this protrusion or depression, it is possible to prevent a backward insertion. Moreover, by providing the mating portion with a switch to turn on the driving power supply, it is possible to operate the switch only when the sensor is inserted in the proper direction.

While in the above embodiments the backward insertion prevention protrusions were located at the side of the sensor, the same effect can be obtained by placing this protrusion on the upper or lower surface of the sensor. Also, the location of the depression to be provided on the sensor is not limited to those shown in the said embodiments.

What is claimed is:

1. A biosensor having a base with a front end, a back end, and two sides, wherein said front end is for insertion into a connector comprising an alignment control protrusion only on one of the sides of the base, wherein the base has at least a working electrode and a counter electrode together with leads connected to each of said electrodes, said alignment control means being separate from said electrodes and said leads.

2. A biosensor measuring apparatus comprising:
a connector freely supporting a biosensor, the biosensor having a base with a front end, a back end, and two sides, wherein said front end is for insertion into a connector, said biosensor having an alignment control means including a protrusion only on one of the sides of the base, the base also having at least a working electrode and a counter electrode together with leads connected to each of said electrodes, said alignment control means being separate from said leads and said electrodes;

a driving power supply to supply a voltage to the said biosensor;

signal processing means to process the current from the electrodes of said biosensor;

display means to display the output of said signal processing means; and, mechanical switching means to turn on said driving power supply when said biosensor is inserted in a specified direction in a support means.

3. A biosensor measuring apparatus as claimed in claim 2, wherein said connector having a wall surface which contacts said protrusion when said biosensor is inserted in the specified direction and contacts a tip portion of said biosensor when inserted in the opposite direction.

4. A biosensor comprising:

a base having a working electrode and a counter electrode disposed on a surface of the base, the base also having respective leads connected to each of the electrodes, the base also having a front end, a back end and two sides wherein the front end is for insertion into a connector, the base also having an alignment control protrusion only on one of the sides thereof for ensuring proper insertion of the biosensor into a receiving apparatus;

a spacer disposed on the surface of the base, the spacer having a slot for defining a specimen supply aperture to provide a specimen with direct access to the electrodes; and a cover disposed so to sandwich the spacer between itself and the base, the cover having a hole which overlays a portion of the slot to allow air to escape when the specimen enters the specimen supply aperture.

5. The biosensor of claim 4 wherein the spacer and the cover have approximately the same dimensions and the base extends beyond the dimensions of the spacer and cover in order to expose the leads disposed thereon.

6. A biosensor measuring apparatus comprising:

a connector having an alignment control protrusion;

a biosensor having an alignment control slot disposed off-center in a front end of a base for mating with the alignment control protrusion of the connector to ensure proper insertion of the biosensor in the connector, the biosensor having at least a working electrode and a counter electrode together with leads connected to each of said electrodes;

a driving power supply to supply a voltage to the biosensor;

signal processing means to process the current from the electrodes of said biosensor;

display means to display the output of said signal processing means; and, mechanical switching means disposed to turn on said driving power supply only when said biosensor is properly inserted into the connector.

* * * * *